United States Patent
Mao et al.

(10) Patent No.: US 10,031,240 B2
(45) Date of Patent: Jul. 24, 2018

(54) AIR KERMA CONVENTIONAL TRUE VALUE DETERMINING METHOD

(71) Applicant: INSTITUTE OF NUCLEAR PHYSICS AND CHEMISTRY, CHINA ACADEMY OF ENGINEERING PHYSICS, Sichuan (CN)

(72) Inventors: Benjiang Mao, Sichuan (CN); Yixin Liu, Sichuan (CN); Yang Xu, Sichuan (CN); Meng He, Sichuan (CN); Renhong Zhuo, Sichuan (CN); Dezhi Wen, Sichuan (CN); Dajie Ding, Sichuan (CN); Jing Cheng, Sichuan (CN); Hui Zheng, Sichuan (CN)

(73) Assignee: INSTITUTE OF NUCLEAR PHYSICS AND CHEMISTRY, CHINA ACADEMY OF ENGINEERING PHYSICS, Mianyang (CN)

( * ) Notice: Subject to any disclaimer, the term of this patent is extended or adjusted under 35 U.S.C. 154(b) by 0 days.

(21) Appl. No.: 15/529,554

(22) PCT Filed: Jun. 1, 2015

(86) PCT No.: PCT/CN2015/000373
§ 371 (c)(1),
(2) Date: May 25, 2017

(87) PCT Pub. No.: WO2016/082294
PCT Pub. Date: Jun. 2, 2016

(65) Prior Publication Data
US 2017/0322315 A1   Nov. 9, 2017

(30) Foreign Application Priority Data

Nov. 26, 2014 (CN) .......................... 2014 1 0697524

(51) Int. Cl.
*G01T 1/00* (2006.01)
*G01T 1/02* (2006.01)
*G01N 23/20* (2018.01)

(52) U.S. Cl.
CPC ............... *G01T 1/02* (2013.01); *G01N 23/20* (2013.01); *G01N 2223/05* (2013.01); *G01N 2223/638* (2013.01)

(58) Field of Classification Search
CPC ....... G01N 2223/419; G01N 2223/612; G01N 23/046; G01N 2223/05; G01N 2223/638; G01N 23/20; G01T 1/02
(Continued)

(56) References Cited

U.S. PATENT DOCUMENTS 7,488,956 B2   2/2009   Douysset
7,597,476 B2   10/2009  Neumann
(Continued)

FOREIGN PATENT DOCUMENTS

CN   102879794 A   1/2013
CN   203385866 U   1/2014
EP   0979027 A2    2/2000

OTHER PUBLICATIONS

Chinese National Standard (2000). X and gamma reference radiation for calibrating dosemeters and doserate meters and for determining their response as a function of photon energy—Part 1: Radiation characteristics and production methods. GB/T 12162.1-2000: 1-37.
(Continued)

*Primary Examiner* — Taeho Jo
(74) *Attorney, Agent, or Firm* — Caesar Rivise, PC

(57) ABSTRACT

An air kerma conventional true value determining method is provided, which addresses the problem of on-site and in-situ verification or calibration of radiation protection with exist-
(Continued)

ing standard reference radiation, which is large in spatial volume and unable or difficult to be moved. The method includes establishing a minitype reference radiation, selecting a proper radiation source and source intensity for providing incident rays for a shielding box, selecting a plurality of gamma ray dosimeters as samples for training a prediction model to obtain the prediction model of the air kerma conventional true value of a point of test, putting a probe of a dosimeter being verified at the point of test, recording scattering gamma spectrum measured by a gamma spectrometer, with the spectrum applied as input to the prediction model to obtain the air kerma conventional true value. The results are accurate and the reference radiation is small in size.

11 Claims, 3 Drawing Sheets

(58) Field of Classification Search
USPC ........................................................ 250/395
See application file for complete search history.

(56) References Cited

U.S. PATENT DOCUMENTS

| | | | | |
|---|---|---|---|---|
| 9,012,834 | B2* | 4/2015 | Yeh | G01T 1/02 250/252.1 |
| 2013/0277563 | A1* | 10/2013 | Giarmana | G01T 1/02 250/366 |
| 2014/0042309 | A1* | 2/2014 | Yeh | G01T 1/02 250/252.1 |
| 2014/0131583 | A1* | 5/2014 | Giarmana | G01T 7/00 250/367 |

OTHER PUBLICATIONS

Chinese National Standard (2004). X and gamma reference radiation for calibrating dosemeters and doserate meters and for determining their response as a function of photon energy—Part 2: Dosimetry for radiation protection over the energy ranges 8 keV to 1.3 MeV and 4 MeV to 9 MeV. GB/T 12162.2-2004: 1-23.
Chinese National Standard (2003). X and gamma radiation dose equivalent (rate) meters and monitors used in radiation protection. JJG 393-2003: 1-20.
International Electrotechnical Commission (2002). Radiation protection instrumentation—Ambient and/or directional dose equivalent (rate) meters and/or monitors for beta, X and gamma radiation. International Standard. CEI IEC 60846 Second Edition: 1-51.
International Organization for Standardization (1996). X and gamma reference radiation for calibrating dosemeters and doserate meters and for determining their response as a function of photon energy—Part 1: Radiation characteristics and production methods. International Standard. ISO 4037-1 First Edition: 1-46.
International Organization for Standardization (1997). X and gamma reference radiation for calibrating dosemeters and doserate meters and for determining their response as a function of photon energy—Part 2: Dosimetry for radiation protection over the energy ranges 8 keV to 1,3 MeV and 4 MeV to 9 MeV. International Standard. ISO 4037-2 First Edition: 1-34.
Liu et al. (2016). Determination of the conventional true value of gamma-ray air kerma in a minitype reference radiation. Applied Radiation and Isotopes, 118, 238-245.
English language abstract for CN 102879794 A (2013).
English language abstract for CN 203385866 U (2014).
International Search Report from corresponding PCT/CN2015/000373 dated Sep. 8, 2015.

* cited by examiner

US 10,031,240 B2

AIR KERMA CONVENTIONAL TRUE VALUE DETERMINING METHOD

CROSS-REFERENCE TO RELATED APPLICATIONS

This application is the U.S. National Phase Application of PCT/CN2015/000373 filed Jun. 1, 2015, which claims priority to CN 201410697524.0 filed Nov. 26, 2014, the contents of which applications are incorporated herein by reference in their entirety for all purposes.

TECHNICAL FIELD

The present invention relates to the field of verification or calibration of radiation protection, and particularly relates to an air kerma conventional true value determining method.

BACKGROUND OF THE INVENTION

Gamma ray dose (rate) meters and dose equivalent (rate) meters are widely used in military, national defense and civil fields, are extremely important tools for guaranteeing the security of nuclear facilities, gamma ray devices, relative workers and the public. To ensure the accuracy and reliability of performance and measured values thereof, they should be verified or calibrated periodically according to the Metrology Law of the People's Republic of China and correlative regulations.

Gamma dose (rate) meters should be verified and calibrated on gamma air kerma secondary standard devices containing secondary standard reference radiation constituted by isotope radiation sources according to the requirements of the national standard GB/T 12162.1-2000 "X and gamma reference radiation for calibrating dose meters and dose rate meters and for determining their response as a function of photon energy—Part 1:—Radiation characteristics and production methods", GB/T12162.2-2004 "X and gamma reference radiation for calibrating dose meters and dose rate meters and for determining their response as a function of photon energy, Part 2: Dosimetry for radiation protection over the energy ranges 8 keV to 1.3 MeV and 4 MeV to 9 MeV", and JJG393-2003 "Verification Regulation of X and Gamma Radiation Dose Equivalent (Rate) Meters and Monitors Used in Radiation Protection". In the process of the verification and calibration work, a secondary standard reference radiation should be verified by using an air kerma measurement standard instrument to obtain the air kerma conventional true value at the point of test of the secondary standard reference radiation; then the reference point disposed on the probe of the dosimeter being verified is accurately positioned in the secondary standard reference radiation as required. And measurement is performed to obtain the calibration factor $$K = \frac{\dot{K}_{air,c}}{\dot{M}_c'},$$

wherein, $\dot{K}_{air,c}$ is the gamma air kerma (rate) measured or calculated by the standard instrument at the experiment point of the secondary standard reference radiation, i.e., the conventional true value of gamma air kerma (rate) at the experiment point, and $\dot{M}_c$ is the indicate value of the dosimeter being verified.

When a gamma air kerma secondary standard device is built, the dimension of reference radiation influencing the dose value, the scattering rays from the shielding wall and the ground, the radiation area of the ray beams, and the non-uniformity of the irradiation area should be designed scientifically, and be tested and verified through detailed experiments, so as to check whether the standard reference radiation meets the requirements. In accordance with relevant standards, the dimension of the standard reference radiation meeting above requirements shall not be smaller than 4 m×4 m×3 m, and the dose rate of gamma rays of the isotope radiation source shall cover the range from μGy/h to mGy/h. Such standard reference radiation cannot be removed no matter in volume or in weight including a shielding building or the like, which leads that all gamma ray dosimeters must be delivered to metrology technology institutions possessing standard reference radiation at fixed sites for verification or calibration. Dosimeters, for the purposes of radiation security monitoring on nuclear power plant reactors and relevant nuclear facilities, are impossible or difficult to be dismounted, and cannot be periodically verified or calibrated by scientific methods and technologies and proper devices yet. Thus it brings hidden danger for radiation security.

One way to realize on-site and in-situ verification or calibration for gamma ray dosimeters is to reduce the spatial volume and the weight of an at least 4 m×4 m×3 m standard reference radiation, which prescribed by the standards, till dismount facilitated. However, reducing the spatial volume of the reference radiation inevitably leads to increase of scattering components in the radiation. Thus the dose contribution rate of the scattered rays in the minitype reference radiation exceeds 5%, which does not comply with the requirements of existing standards, influences response of the dosimeter and results a calibration error.

SUMMARY OF THE INVENTION

In order to solve the problem that there is no scientific or proper method for verifying and calibrating gamma ray dosimeters, the present invention provides an air kerma conventional true value determining method which is characterized by including the following steps:

Step 1, establishing a minitype reference radiation (MRR), which contains a shielding box with a dimension no more than 1.5 meters and a gamma spectrometer, the shielding box being positioned horizontally, an incident hole being set on its side for incidence of incident rays, a point of test being set in the shielding box in the direction of the incident rays, a test hole being set on its upper surface, through which the probe of a dosimeter being verified can be put into the shielding box, the reference point of the probe being coincided with the point of test, the shielding box being segmented into two parts by a plane perpendicular to the connecting line of the incident hole and the point of test, and a monitor point being set in the shielding box and located at the part adjacent to the incident hole, and at the position not directly irradiated by the incident rays, a gamma spectrometer being arranged in the shielding box, the reference point on the probe thereof being coincided with the monitor point and being fixed in the shielding box.

Step 2, selecting a proper radiation source and source intensity to provide incident rays for the shielding box;

Step 3, selecting a plurality of gamma ray dosimeters as samples for training a prediction model to obtain the prediction model of the air kerma conventional true value at the point of the test;

Step 4, putting the probe of the dosimeter being verified at the point of test, then measuring the scattering gamma spectrum with a gamma spectrometer, with the prediction model and the gamma spectrum as input, the air kerma conventional true value at the point of test is obtained.

Specifically, step 3 includes the following specific steps:

Step 31, selecting a plurality of gamma ray dosimeters as samples for training a prediction mode of the air kerma conventional true value in MRR;

Step 32, measuring the air kerma conventional true value at the point of test when no sample dosimeter is put, then coinciding the reference point of the probe of the sample dosimeter with the point of test, measuring the air kerma conventional true value at the point of test through an instrument transfer method, and measuring the scattering gamma spectrum of the monitor point by a gamma spectrometer.

Step 33, extracting the dose feature components from the gamma spectrum through a principal component analysis method.

Step 34, training a prediction model of the air kerma conventional true value at the point of test through a support vector machine regression method.

Further, step 32 includes the following specific steps:

Step 32A, putting a standard graphite cavity ionization chamber at the point of test, and measuring the air kerma conventional true value $K_j'$ at the point of test when the intensity of an incident ray beam is $V_j$;

Step 32B, putting the reference point of the probe of the $i^{th}$ sample dosimeter at the point of test, setting the intensity of the incident ray beam as $V_j$, and then recording the indicate value of the sample dosimeter as $R_{ij}$ and measuring the gamma spectrum $S_{ij}$ at the monitor point with a gamma spectrometer;

Step 32C, putting the sample dosimeter in the standard reference radiation to search a point where the indicate value of the dosimeter is $R_{ij}$, the corresponding air kerma conventional true value of the point is equal to the air kerma conventional true value $K_{ij}$ at the point of test in the MMR;

Step 32D, sequentially putting the reference points of the probes of the x sample dosimeters at the point of test, and repeating steps 32A to 32C under the conditions of y source intensities to obtain x×y sets of $K_1$, $S_{ij}$ and $K_j'$ data for training the model of the function relationship $K_{ij}=f_1(S_{ij}, K_j')$.

Specifically, step 33 includes the following steps:

Step 33A, dispersing each $S_{ij}$ with a proper energy interval $\Delta E$ to obtain a counting rate array $\eta_{ijn}$ corresponding to the different energies of the scattering gamma rays, then constructing the n-dimensional vectors $a_{ij}$ of the counting rates related to different scattering gamma ray energies;

Step 33B, constructing a scattering gamma spectrum counting rate sample data matrix $\Phi_{(x \times y) \times n}$ through the experiments of the probes of the x sample dosimeters under the conditions of y source intensities in step 32D;

Step 33C, extracting principle components of the n-dimensional vectors $a_{ij}$ with a principal component analysis method to obtain the principle component vectors $\Psi_{ij}=T_{n \times m}^T \cdot a_{ij}$ of the n-dimensional vectors $a_{ij}$, wherein m≤n, $T_{n \times m}^T$ is a transposition of $T_{n \times m}$, and $T_{n \times m}$ is obtained from the covariance matrix $\xi_{n \times n}$ of $\Phi_{(x \times y) \times n}$, and it is the score matrix constructed by the first m eigenvector of $\xi_{n \times n}$;

Step 33D, obtaining a function relationship $\Psi_{ij}=f_2(S_{ij})$ between $\Psi_{ij}$ and $S_{ij}$, and thereby obtaining a model $K_{ij}=f_3(\Psi_{ij}, K_j')=f_3[f_2(S_{ij}), K_j']$.

Further, in step 33A, the proper energy interval $\Delta E$ refers to:

$\Delta E=1500/(128 \times 2^z)$ keV, wherein 0≤z≤4, z is an integer.

Specifically, step 33C includes the following specific steps:

Step 33C1, obtaining a covariance matrix $\xi_{n \times n}$ from $\Phi_{(x \times y) \times n}$, and solving n eigenvalues $\lambda_1 \geq \lambda_2 \geq \ldots \geq \lambda_n \geq 0$ of the covariance matrix $\xi_{n \times n}$ and the corresponding eigenvectors $t_1, \ldots, t_m, \ldots t_n$;

Step 33C2, obtaining a score matrix $T_{n \times m}(t_1, \ldots, t_m)$ of the principal components, wherein m is determined by formula $\Sigma_{k=1}^m \lambda_k / \Sigma_{k=1}^n \lambda_k \geq \delta_m$, $\delta_m \geq 85\%$;

Step 33C3, obtaining the principal component vectors $\Psi_{ij}=T_{n \times m}^T \cdot a_{ij}$ of the n-dimensional vectors $a_{ij}$, wherein m≤n, and $T_{n \times m}^T$ is a transposition of $T_{n \times m}$.

Still further, step 34 includes the following steps:

Step 34A, obtaining a data matrix sample $(K_{ij}, \Psi_{ij}, K_j')_{(x \times y) \times (m+2)}$ through the experiments of the probes of the x sample dosimeters under the y kinds of $V_j$ conditions in step 32D, and obtaining a prediction model $K_{ij}=f_3(\Psi_{ij}, K_j')$ of $K_{ij}$ by a support vector machine regression method.

Specifically, in step 34A, the specific method for obtaining a prediction model $K_{ij}=f_3(\Psi_{ij}, K_j')$ of $K_{ij}$ by adopting a support vector machine regression method includes the steps as follows: radial basis function being selected as the kernel function in the model training process. Parameters of the kernel function being determined by a cross validation method, in the training process, the sample data $(K_{ij}, \Psi_{ij}, K_j')_{(x \times y) \times (m+2)}$ being divided into training sets and testing sets according to a proper proportion; and when test error is not more than 5%, ending the training, and determining the prediction model $K_{ij}=f_3(\Psi_{ij}, K_j')$.

Still further, the proper proportion refers to that the proportion of the training set to the testing set is more than or equal to 1:1.

Specifically, step 4 includes the following steps:

Step 41, putting the reference point of the probe of the dosimeter being verified at the point of test of test;

Step 42, selecting a proper radiation source and putting it into an isotope radiation source accommodating device, and adjusting attenuation rate to obtain the proper intensity $V_j$ of the incident ray beam;

Step 43, measuring the scattering gamma spectrum with a gamma spectrometer. with the prediction model $K_{ij}=f_3(\Psi_{ij}, K_j')=f_3[f_2(S_{ij}), K_j']=f_1(S_{ij}, K_j')$ and the gamma spectrum as input, and the air kerma conventional true value at the point of test in the MRR is obtained.

The beneficial effects of the present invention are that when determining the air kerma conventional true value in a minitype reference radiation with a prediction model $K_{ij}=f_1(S_{ij}, K_j')$, PCA reasonably extracts the feature components which characterize the dose features in the MRR well. Meanwhile the dimension of sample data applied for model training is reduced significantly and the model training efficiency is improved. SVM, as a multivariate linear regression method, is suitable for small sample modeling. The compatibility of the prediction model trained by SVM, the accuracy of the prediction value and the universality of the model are excellent. The method deducts the disturbance from the scattering gamma rays caused by the minitype reference radiation and probe in determining the air kerma conventional true value at the point of test. The air kerma conventional true value determined by the method is equal to that determined according to national standards GB/T 12162.1-2000, GB/T 12162.2-2004 and JJG393-2003. Based on the determination method present in this invention, verification or calibration devices and equipment for radiation protection dosimeters with proper weight and volume can be designed and manufactured as skid-mounted, vehicle-mounted, hand-propelled or other removable type, which are suitable for the in-situ verification or calibration of various gamma ray dosimeters and security monitoring dosimeters.

Among them, 1 is a shielding box, 2 is a dosimeter being verified, 3 is incident rays, 4 is a radiation source, 5 is a test hole, 6 is a point of test, 7 is a monitor point, 8 is an incident hole, and 9 is a gamma spectrometer.

DETAILED DESCRIPTION OF THE EMBODIMENTS

The technical solution of the present invention will be described in detail below in combination with the embodiment and the accompanying drawings.

An air kerma conventional true value determining method of the present invention is that: firstly, establishing a minitype reference radiation (MRR), which comprises a shielding box and a gamma spectrometer. The shielding box is positioned horizontally and an incident hole is set on the side thereof for incidence of incident rays. The point of test is set in the direction of the incident rays in the shielding box. There is also a test hole on the upper surface of the shielding box, by which the probe of a dosimeter being verified can be put into the shielding box. The reference point of the probe should be coincided with the point of test. Further a monitor point is set in the shielding box. The shielding box is segmented into two parts by one plane perpendicular to the connecting line of the incident hole and the point of test. The monitor point is located at the part adjacent to the incident hole in the shielding box where directly irradiate incident rays are avoided. A gamma spectrometer is disposed in the shielding box. The reference point on the probe of the spectrometer is coincided with the monitor point and the probe is fixed in the shielding box. Next, a proper radiation source and source intensity being selected to provide incident rays for the shielding box. And then a plurality of gamma ray dosimeters to be selected as samples for training a prediction model of the air kerma conventional true value at the point of test. Lastly, the probes of dosimeters being verified are arranged at the point of test, then measuring the scattering gamma spectrum with a gamma spectrometer, with the prediction model and the gamma spectrum as input, the air kerma conventional true value at the point of test is obtained.

The Embodiment

Figure 1:
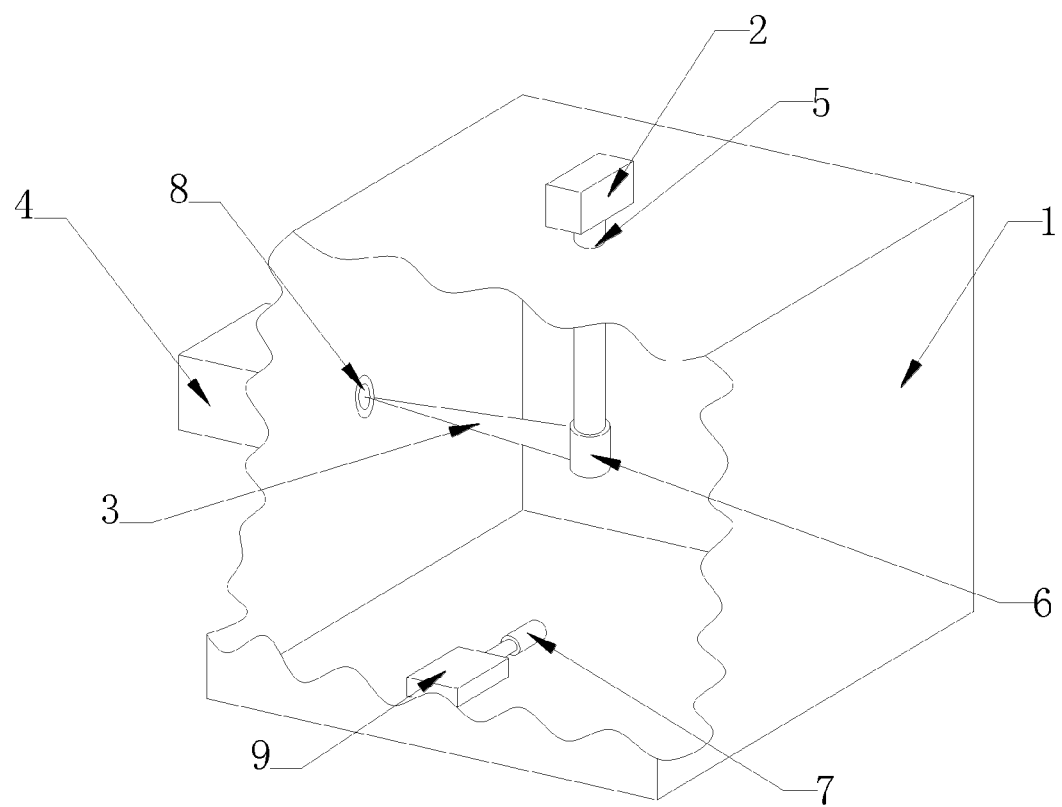
FIG. 1 is a structural schematic diagram of a minitype reference radiation in an embodiment of the present invention.

In this embodiment, the structural schematic diagram of the minitype reference radiation (MRR) is shown as FIG. 1, the minitype reference radiation comprises a shielding box 1 with a dimension not more than 1.5 meters and a gamma spectrometer 9. The shielding box 1 is positioned horizontally and provided with an incident hole 8 on the side thereof for the incidence of incident rays 3. A point of test 6 is arranged in the direction of the incident rays 3 in the shielding box 1, a test hole 5 is further provided on the upper surface of the shielding box 1, by which a probe of an dosimeter 2 being verified can be put into the shielding box 1 and can make the reference point of the probe being coincided with the point of test 6. A monitor point 7 is further arranged in the shielding box 1, the shielding box 1 is segmented into two parts by one plane that is perpendicular to the connecting line of the incident hole 8 and the point of test 6, and the monitor point 7 is located at the part adjacent to the incident hole 8 in the shielding box 1 and at the position not directly irradiated by the incident rays 3. The gamma spectrometer 9 is disposed in the shielding box 1. The reference point on the probe thereof is coincided with the monitor point 7, and is fixed in the shielding box 1.

In this embodiment, the shielding box 1 could be a cube with a sectional size of 1 meter, e.g., a 1 m×1 m×1 m sized cube, and could also be a cuboid or in other shape, the specific size being determined by the total weight of the MRR which allowed by the intended use. The incident hole 8 could be located in the center position of the side of the shielding box, the point of test 6 could also be located in the geometrical center of the shielding box, and the monitor point 7 is generally located at the inner bottom of the shielding box 1.

In use, the specific method includes the following steps:

Step 1, establishing the aforesaid minitype reference radiation device.

Step 2, selecting a proper radiation source and source intensity for providing incident rays for the shielding box.

Step 3, selecting a plurality of gamma ray dosimeters as samples for training a prediction model of the air kerma conventional true value at the point of test in the MRR.

This step includes the following specific steps:

Step 31, selecting a plurality of gamma ray dosimeters as samples for training a prediction model of the air conventional true value, and the types of the plurality of selected gamma ray dosimeters can be BH3103A, FJ317E, SSM-1, FD-3013B, CIT-2000FX·γ, Inspector1000 and Canberra Radiagem2000;

Step 32, measuring the air kerma conventional true value at the point of test when no sample dosimeter is arranged, coinciding the reference point of the probe of a sample dosimeter with the point of test, then measuring the air kerma conventional true value at the point of test by adopting an instrument transfer method, measuring the scattering gamma spectrum of the monitor point by a gamma spectrometer, The specific method is as follows:

Step 32A, putting a standard graphite cavity ionization chamber at the point of test, and measuring the air kerma conventional true value $K_j$ at the point of test, when the intensity of an incident ray beam is $V_j$;

Step 32B, putting the reference point of the probe of the $i^{th}$ sample dosimeter at the point of test, setting the intensity of the incident ray beam as $V_j$, recording the indicate value of the sample dosimeter $R_{ij}$ and measuring the gamma spectrum $S_{ij}$ at the monitor point with a gamma spectrometer;

Step 32C, putting the sample dosimeter in the standard reference radiation to search a point where the indicate value of the dosimeter is $R_{ij}$, the air kerma conventional true value corresponding to the point being the air kerma conventional true value at the point of test $K_{ij}$;

Step 32D, sequentially putting the reference points of the probes of the x sample dosimeters in the point of test, repeating steps 32A to 32C under y kinds of $V_j$ conditions to obtain x×y groups of $K_{ij}$, $S_{ij}$ and $K_j'$ data, and obtaining the function relationship $K_{ij}=f_1(S_{ij},K_j')$ thereof;

Step 33, acquiring a dose feature value by adopting a principal component analysis method according to the gamma spectrum. The specific method is as follows:

Step 33A, dispersing each acquired $S_{ij}$ according to a certain energy interval ΔE to obtain a counting rate $\eta_{ijn}$ array corresponding to the energies of the scattering gamma rays, and constructing n-dimensional vectors $a_{ij}$ of the counting rates using the energies of the scattering gamma rays as research objects; here, the certain energy interval ΔE refers to $\Delta E=1500/(128\times 2^z)$ keV, and z is an integer more than or equal to 0 and less than or equal to 4;

Step 33B, constructing a scattering gamma spectrum counting rate data matrix sample $\Phi_{(x\times y)\times n}$ via the experiments of the probes of the x sample dosimeters under the y kinds of $V_j$ conditions in step 32D;

Step 33C, Extracting the principal components of the n-dimensional vectors $a_{ij}$ by adopting a principal component analysis method to obtain the principal component vectors $\Psi_{ij}=T_{n\times m}^T\cdot a_{ij}$ of the n-dimensional vectors $a_{ij}$, wherein m≤n, $T_{n\times m}^T$ is a transposition of $T_{n\times m}$, and $T_{n\times m}$ refers to a covariance matrix $\xi_{n\times n}$ obtained from $\Psi_{(x\times y)\times n}$; and solving a score matrix composed of m first feature vectors of the covariance matrix $\xi_{n\times n}$. The specific method is as follows:

Step 33C1, obtaining a covariance matrix from $\Phi_{(x\times y)\times n}$, and solving n feature values $\lambda_1\geq\lambda_2\geq\ldots\geq\lambda_n\geq 0$ of the covariance matrix $\xi_{n\times n}$ and corresponding feature vectors $t_1,\ldots,t_m,\ldots t_n$;

Step 33C2, a score matrix of the principal components is $T_{n\times m}=(t_1,\ldots,t_m)$, wherein m is determined by formula $\Sigma_{k=1}^m\lambda_k/\Sigma_{k=1}^n\lambda_k\geq\delta_m$, and $\delta_m\geq 85\%$;

Step 33C3, the principal component vector of the n-dimensional vectors $a_{ij}$ is $\Psi_{ij}=T_{n\times m}^T\cdot a_n$, wherein m≤n, and $T_{n\times m}^T$ is a transposition of $T_{n\times m}$;

Step 33D, obtaining the function relationship $\Psi_{ij}=f_2(S_{ij})$ between $\Psi_{ij}$ and $S_{ij}$, thus obtaining $K_{ij}=f_3(\Psi_{ij},K_j')=f_3[f_2(S_{ij}),K_j']$;

Step 34, obtaining a prediction model of the air kerma conventional true value at the point of test by adopting a support vector machine method. The specific method is as follows:

Step 34A, obtaining a data matrix sample $(K_{ij},\Psi_{ij},K_j')_{(x\times y)\times(m+2)}$ via the experiments of the probes of the x sample dosimeters under the y kinds of $V_j$ conditions in step 32D, and obtaining a prediction model $K_{ij}=f_3(\Psi_{ij},K_j')$ of $K_{ij}$ by adopting a support vector machine regression method. The specific method is as follows: training a kernel function selected by a regression prediction model as a radial basis kernel, the parameter of the kernel function is determined by a cross validation method; when the model is established, allocating the data samples $(K_{ij},\Psi_{ij},K_j')_{(x\times y)\times(m+2)}$ to a training set and a testing set according to a certain proportion; and when the test error is not more than 5%, ending the training, and determining the prediction model as $K_{ij}=f_3(\Psi_{ij},K_j')$. Herein, the certain proportion refers to that the proportion of the training set to the testing set is more than or equal to 1:1.

Step 4, putting the probe of the dosimeter being verified at the point of test, then monitoring the scattering gamma spectrum with a gamma spectrometer, according to the prediction model, the air kerma conventional true value at the point of test is obtained;

Step 4 includes the following specific steps:

Step 41, putting the reference point of the probe of the dosimeter being verified at the point of test of test;

Step 42, selecting a proper radiation source and putting it into an isotope radiation source accommodating device, and adjusting attenuation rate to obtain the proper intensity $V_j$ of the incident ray beam;

Step 43, measuring the scattering gamma spectrum with a gamma spectrometer, inputting the gamma spectrum to the prediction model $K_{ij}=f_3(\Psi_{ij},K_j')=f_3[f_2(S_{ij}),k_j']=f_1(S_{ij},K_j')$, and the air kerma conventional true value at the point of test in the MRR is obtained.

The method may further include the following step:

Obtaining a correction factor $\omega=K_{ij}/R_{ij}$ in combination with the indicate value $R_{ij}$ of the dosimeter being verified.

The energy response characteristic of the dosimeter being verified can also be obtained via the above method by switching the radiation sources with different energies; or the angle response data of dosimeter being verified can be obtained by rotating the probe thereof, and other verification items stipulated in JJG393-2003 can also be realized.

A specific example is as follows:

A radioisotope source $^{137}$Cs is selected as the radiation source 4 in this embodiment to provide a radiation ray source for the minitype reference radiation (MRR), and a calibration device for calibration of a gamma ray radiation protection instrument is constructed, the structure thereof being shown in FIG. 1. According to the requirement of radiation protection, the shielding box is made of a material such as lead, tungsten alloy or the like with a proper thickness, thus ensuring personnel security when the device is used.

The shielding box 1 is in the shape of a cube having a side length of 1 m, and the geometric center thereof is set as a point of test 12. The incident hole 8 having the diameter of 120 mm and used for the incidence of gamma rays is arranged in the geometric center of the side which is close to the radiator (the radiation source 4), of the shielding box 1. The shielding box 1 is segmented into two parts by one plane that is perpendicular to the connecting line of the incident hole 8 and the point of test 6, and the monitor point 7 is located at the part adjacent to the incident hole 8 on the bottom center line of the shielding box 1 and spaced 100 mm from the projection point at the point of test 6 on the bottom; the test hole 5 having the diameter of 200 mm is arranged at the top of the shielding box 1, and is used for putting the probe of the instrument 2 being verified; scattering gamma ray spectrum in the box are measured by an Inspector1000 portable gamma spectrometer of Canberra company, the reference point of the probe of the gamma spectrometer 9 is aligned with the monitor point 7 on the bottom of the shielding box 1, and the probe of the gamma spectrometer 9 is fixed.

The activity degree of the $^{137}$Cs radioisotope source is 1 Ci, the incident ray beam 3 is provided for the shielding box 1 via the device 4 such as a radiator or the like, and the attenuation times of the incident ray beam 3 is adjusted according to the source intensity of the radiation source and the range of the dosimeter being verified. The times of an attenuator is adjusted according to the range of common gamma ray dose (rate) meter and dose equivalent (rate) meter to obtain five experiment source intensities $V_j$, (j=1, 2, ..., 5), and the range of the dose rate is 65 μGy/h-1.25 mGy/h.

An experiment is carried out according to the method of this embodiment, a prediction model of the air kerma conventional true value at the point of test 6 is obtained, and the specific implementation steps are as follows:

Step A

A PTW-32005 standard graphite cavity ionization chamber is arranged at the point of test 6 of the shielding box, and the air kerma value at the point of test 6 $K_j'$ is measured when the source intensity is $V_j$.

Step B

Totally nine different types of common gamma ray dose (rate) meters BH3103A, FJ317E, SSM-1, FD-3013B, CIT-2000FX-γ, Inspector1000 (containing two kinds of probes: an IPRON-3 probe and an IPROS-2 probe) and Canberra Radiagem2000 are selected as samples for the experiment, and consecutively numbered as 1, 2 . . . 9, i.e., i=1 . . . 9.

Step C

Figure 2:
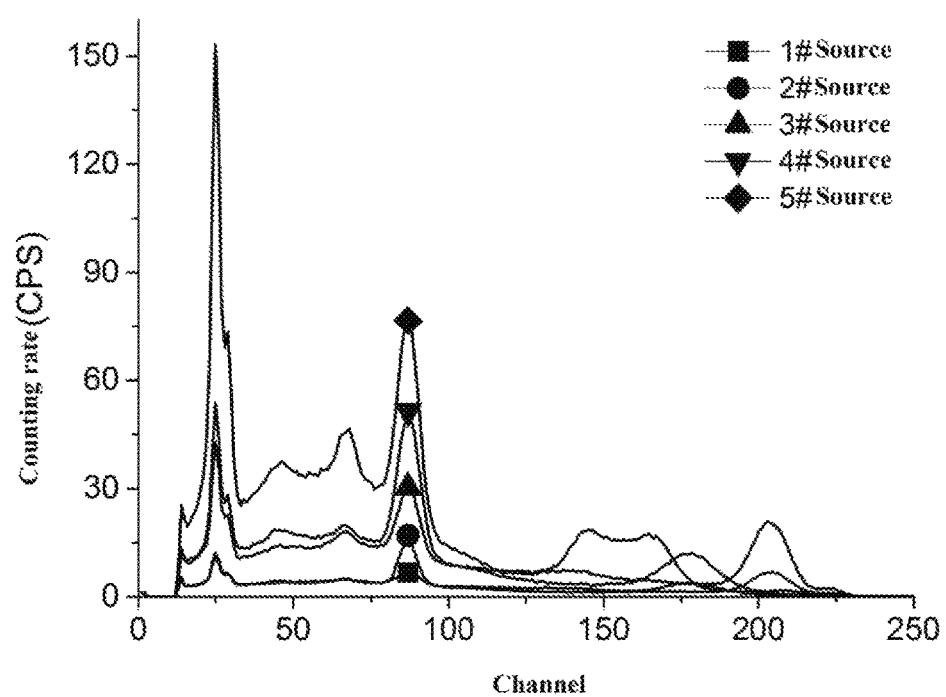
FIG. 2 is a scattering gamma spectrum at a monitor point when dosimeter BH3103A in MMR in the embodiment of the present invention.

The probe of the above No. 1 instrument is vertically arranged into the shielding box. And the reference point on the probe is coincided with the point of test 6. The source intensity $V_j$ is sequentially switched for measurement, and recording the indicate value $R_{1j}$ of No. 1 instrument and the gamma spectrum $S_{1j}$ recorded by the Inspector1000. FIG. 2 shows the scattering gamma spectrum of No. 1 instrument $S_{1j}$ in the shielding box under five different intensities $V_j$.

Step D

The No. 1 instrument is arranged in the standard radiation of "γ-ray air kerma (protection level) measurement standards" of an ionizing radiation metrology station of China Academy of Engineering Physics to search a point $P_{1j}$ having the indicate value $R_{1j}$. The air kerma conventional true value at the point $P_{1j}$ is obtained according to the existing parameters of the standard radiation. And the value is the air kerma conventional true value $K_{1j}$ at the point of test 6 of the shielding box when the probe of No. 1 instrument is arranged at the point of test 6 of the shielding box under the source intensity $V_j$ in step C.

Step E

The probes of No. 2 to No. 9 instruments are respectively arranged at the point of test 6 in the shielding box, and 45 groups of $K_{ij}$, $S_{ij}$ and $K_j'$ data can be obtained by repeating steps C and D under five $V_j$ conditions. The data has a function relationship $K_{ij}=f_1(S_{ij},K_j')$, which is a mathematic prediction model for predicting the air kerma conventional true value of the probe of the instrument being verified at the point of test 6 of the shielding box in the method of the present invention.

Step F

Figure 3:
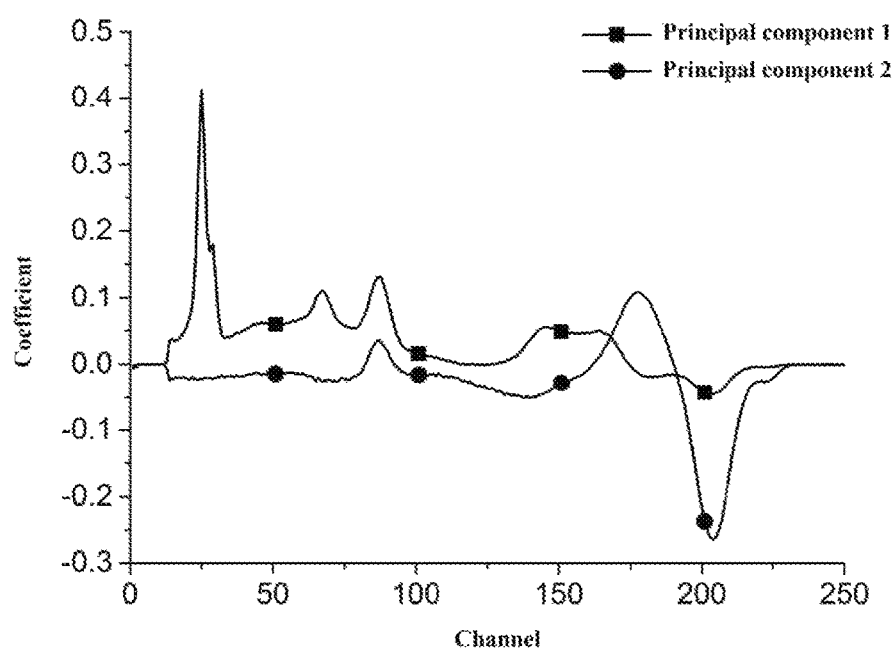
FIG. 3 is a schematic diagram of a linear combination coefficient of principle components extracted from scattering gamma spectrum at the monitor point in the embodiment of the present invention.

The $S_{ij}$ is dispersed according to an energy interval 3 keV to obtain an array of 512 counting rates $\eta_{ijn}$ corresponding to the energies of the scattering gamma rays. According to $S_{ij}$ features, in order to reduce the dimension of calculating data, the first 250 counting rates having obvious features are selected as valid data, and 250-dimensional vectors $a_{ij}$ of the counting rates using the energies of the scattering gamma rays as a research object are constructed. Then a scattering gamma spectrum counting rate data matrix sample $\Psi_{45\times250}$ is constructed via the experimental data of the probes of the nine gamma dose (rate) meters under the five source intensity $V_j$ conditions. The principal components of 45 pieces of 250-dimensional vectors $a_{ij}$ are solved by adopting a principal component analysis (PCA) method, i.e., first a covariance matrix $\xi_{250\times250}$ is obtained from $\Psi_{45\times250}$, and then 250 feature values $\lambda_1\geq\lambda_2\geq \ldots \geq\lambda_{250}\geq0$ of the covariance matrix $\xi_{250\times250}$ and the corresponding feature vectors $t_1, \ldots, t_m, \ldots t_n$ are solved. The score matrix of the principal components is $T_{250\times m}=(t_1, \ldots, t_m)$, wherein m is determined by formula $\Sigma_{k=1}^{m}\lambda_k/\Sigma_{k=1}^{n}\lambda_k\geq\delta_m$. The principal component score matrix of the 250-dimensional vectors $a_{ij}$ is $T_{n\times m}(t_1, \ldots, t_m)$, m≤n. When $\delta_m$ is 90%, m=2. The linear combination coefficient of the score vectors $t_1$ and $t_2$ of two principal components is shown as FIG. 3.

Step G

According to step F, a function relationship $\Psi_{ij}=f_2(S_{ij})$ between $\Psi_{ij}$ and $S_{ij}$ can be obtained. The simulated prediction model $K_{ij}=f_1(S_{ij},K_j')$ in step E can be simplified into $K_{ij}=f_3(\Psi_{ij},K_j')$ by replacing $S_{ij}$ with $\Psi_{ij}$. Moreover, a data matrix sample $(K_{ij},\Psi_{ij},K_j')_{45\times(m+2)}$ can be obtained via experiments by using the nine gamma ray dose (rate) meters under the conditions of five different radiation source intensities $V_j$.

Step H

Based on the data matrix sample $(K_{ij},\Psi_{ij},K_j')_{45\times(m+2)}$ obtained via experiments, a prediction model $K_{ij}=f_3(\Psi_{ij},K_j')$ of $K_{ij}$ is obtained by adopting a least squares support vector machine (LS-SVM, an improved form of SVM) regression method in this embodiment.

The prediction model is trained on a Matlab software platform for the Windows7 system. And the version of the Matlab software is 2012a. A radial basis function $$K(x, x_i) = \exp\left(-\frac{\|x - x_i\|^2}{2\sigma^2}\right)$$

is selected as the kernel function of the model by calling a least squares support vector machine toolbox (LS-SVMlab Toolbox User's Guide version 1.5) in the platform. And the parameter $\sigma^2$ of the kernel function and the regularization parameter c are determined by an L-fold cross validation method. L is set to be equal to 10. And the data sample $(K_{ij},\Psi_{ij},K_j')_{45\times(m+2)}$ is allocated to a training set and a testing set according to a proportion of 6:3. And the training is ended when the test error is less than or equal to 5%. The prediction model of $K_{ij}$ is $K_{ij}=F[(\Psi_{ij},K_j'), (\Psi'',K'')]\times\alpha+b$ is finally acquired, wherein F is the kernel function, a and b are parameters of the model, $\Psi_{ij}$ is the principle component vector of the energy spectrum $S_{ij}$ when the dosimeter being verified is introduced into the shielding box, And $K_j$ is the air kerma value at the point of test of the shielding box when no probe is introduced under the source intensity, $\Psi''$ and $K''$ are sample data of the principle component vector of the energy spectrum for training the model and air kerma sample data at the point of test in the shielding box when no probe is introduced. In combination with the function $\Psi_{ij}=f_2(S_{ij})$, the model can be expressed as $K_{ij}=F[(f_2(S_{ij}),K_j'), (\Psi'',K'')]'\times\alpha+b$, i.e., $K_{ij}=f_1(S_{ij},K_j')$.

When the BH3103A gamma ray dose rate meter 2 being verified is calibrated, a probe of the BH3103A is put into the shielding box, and the reference point of the probe is coincide with the point of test 6 of the MRR; a proper radiation source intensity $V_j$ is determined according to the range of the BH3103A in a manner of selecting an attenuator or the like so that the indicate value of the BH3103A is nearby the midpoint of the calibration range, scattering gamma spectrum measured by the gamma spectrometer 9 are recorded, the principle component vector $\Psi_i$ of the spectrum data is extracted and introduced into the prediction model established $K_{ij}=F[(\Psi_{ij},K_j'), (\Psi'',K'')]'\times\alpha+b$, the air kerma conventional true value $K_{ij}$ at the point of test 6 of the MRR under such condition is 91.27 μGy/h, the mean $\bar{R}$ of indicate values of the five dosimeters is 89.82 μGy/h, a calibration factor is obtained according to formula $$\omega = \frac{K_{ij}}{R} = 1.016,$$

and calibration of the dosimeter is thus realized.

The aforesaid embodiment is only an example for realizing the present invention, and the present invention can be realized in multiple ways. For example, the shape of minitype reference radiation MRR is not limited to a cube, A MRR in other shape such as a cuboid or the like does not influence the effect of the present invention, and the methods of introducing gamma rays via the shielding box and limiting the gamma rays into a small closed space are all implementations of the present invention; the point of test and the monitor point are not limited to the positions in the embodiment, as long as they are located in the MRR, can fulfill the purposes required by the claims and do not influence the effect of the present invention; as for the SVM method for establishing the prediction model $K_{ij}=f_1(S_{ij},K_j')$ of the air kerma conventional true value at the point of test in the MRR, the SVM method has multiple forms and is rapidly developed, the SVM regression mode is not limited to the least squares support vector machine LS-SVM used in this embodiment, and other modes of SVM, C-SVM, v-SVM and the like adopting an SMO (Sequential Minimal Optimization) algorithm are available for fulfilling the purpose of establishing the prediction model $K_{ij}=f_1(S_{ij},K_j')$ of the air kerma conventional true value at the point of test in the MRR.

Other than one $^{137}$Cs cesium source for calibration of the gamma ray dose (rate) dosimeter in this embodiment, $^{137}$Cs, $^{241}$Am and $^{60}$Co sources and the method introduced in the present invention can also be simultaneously adopted to obtain the indicators of energy response, angle response and the like of the gamma ray dose (rate) dosimeter. An X ray machine serving as a ray source and the method of the present invention can also be adopted for verification and calibration of gamma and X ray dose (rate) dosimeters.

Although the content of the present invention has been introduced in detail via the above preferred embodiment, the above introduction shall not be regarded as a limitation to the present invention. It would be obvious for a person having professional knowledge and skills to make various modifications, substitutions and avoidances to the present invention upon reading the above content. Therefore, the protection scope of the present invention should be defined by the appended claims.

The invention claimed is:

1. An air kerma conventional true value determining method, comprising the following steps:
   Step 1, establishing a minitype reference radiation, which comprises a shielding box comprising a side length not more than 1.5 meters, the shielding box being positioned horizontally and an incident hole being provided on a side thereof for incidence of incident rays, a point of test being arranged in a direction of the incident rays in the shielding box, the shielding box being further provided with a test hole on an upper surface through which a probe of an dosimeter being verified can be put into the shielding box, a reference point on the probe coinciding with the point of test, a monitor point being also arranged in the shielding box, the shielding box being segmented into two parts by one plane perpendicular to a connecting line of the incident hole and the point of test, the monitor point being located at a part adjacent to the incident hole in the shielding box and at a position not directly irradiated by the incident rays, a gamma spectrometer being arranged in the shielding box, a reference point on a probe thereof coinciding with the monitor point and the probe being fixed in the shielding box;
   Step 2, selecting a proper radiation source and source intensity to provide incident rays for the shielding box;
   Step 3, selecting a plurality of gamma ray dosimeters as samples for straining a prediction model to obtain the prediction model of the air kerma conventional true value at the point of test; and
   Step 4, putting the probe of the dosimeter being verified at the point of test, measuring a scattering gamma spectrum by the gamma spectrometer, with the prediction model and the gamma spectrum as input, the air kerma conventional true value at the point of the test being obtained.

2. The air kerma conventional true value determining method of claim 1, wherein Step 3 comprises the following specific steps:
   Step 31, selecting a plurality of gamma ray dosimeters as samples for straining a prediction model;
   Step 32, measuring the air kerma conventional true value at the point of test when no sample dosimeter is put, putting a reference point of a probe of an sample dosimeter on the point of test, measuring the air kerma conventional true value at the point of test by adopting an instrument transfer method, and measuring the gamma spectrum of the monitor point via the gamma spectrometer;
   step 33, extracting a dose feature value by adopting a principal component analysis method according to the gamma energy spectra; and
   Step 34, training a prediction model of the air kerma conventional true value at the point of test by adopting a support vector machine regression method.

3. The air kerma conventional true value measuring method of claim 2, wherein step 32 comprises the following specific steps:
   Step 32A, putting a standard graphite cavity ionization chamber at the point of test, and measuring the air kerma conventional true value $K_j'$ at the point of test when the intensity of an incident ray beam is $V_j$;
   Step 32B, putting the reference point of the probe of the $i^{th}$ sample dosimeter at the point of test, setting the intensity of the incident ray beam as $V_j$, recording the indicate value of the sample dosimeter $R_{ij}$ and measuring the gamma spectrum $S_{ij}$ of the monitor point at the moment via the gamma spectrometer;
   Step 32C, putting the sample dosimeter in the standard reference radiation to search a point having the indicate value equal to $R_{ij}$, the corresponding air kerma conventional true value of the point being the air kerma conventional true value $K_{ij}$ at the point of test;
   Step 32D, sequentially putting the reference points of the probes of the x sample dosimeters in the point of test, and repeating steps 32A to 32C under y source intensity conditions to obtain x×y sets of $K_{ij}$, $S_{ij}$ and $K_j'$ data for straining a model of the function relationship $K_{ij}=f_1(S_{ij},K_j')$.

4. The air kerma conventional true value measuring method of claim 3, wherein step 33 comprises the following steps:

Step 33A, dispersing each acquired $S_{ij}$ according to a proper energy interval $\Delta E$ to obtain a counting rate $\eta_{ijn}$ array corresponding to energies of the scattering gamma rays, and constructing n-dimensional vectors $a_{ij}$ of the counting rates using the energies of the scattering gamma rays as a research object;

Step 33B, constructing a scattering gamma spectrum counting rate data matrix sample $\Phi_{(x \times y) \times n}$ via experiments of the probes of the x sample dosimeters under the y source intensity conditions in step 32D;

Step 33C, extracting feature components of the n-dimensional vectors $a_{ij}$ by adopting a principal component analysis method to obtain principal component vectors $\Psi_{ij}=T_{n \times m}^T \cdot a_{ij}$ of the n-dimensional vectors $a_{ij}$, m≤n, $T_{n \times m}^T$ being a transposition of $T_{n \times m}$, and $T_{n \times m}$ referring to obtaining a covariance matrix $\xi_{n \times n}$ from $\Phi_{(x \times y) \times n}$; and solving a score matrix composed of m first feature vectors of the covariance matrix $\xi_{n \times n}$; and Step 33D, obtaining a function relationship $\Psi_{ij}=f_2(S_{ij})$ between $\Psi_{ij}$ and $S_{ij}$, thus obtaining the model $K_{ij}=f_3(\Psi_{ij},K_j')=f_3[f_2(S_{ij}),K_j']$.

5. The air kerma conventional true value determining method of claim 4, wherein in step 33A, the proper energy interval $\Delta E$ refers to: $\Delta E=1500/(128 \times 2^z)$ keV, 0≤z≤4, z being an integer.

6. The air kerma conventional true value determining method of claim 4, wherein step 33C comprises the following specific steps:

Step 33C1, obtaining a covariance matrix $\xi_{n \times n}$ from $\Phi_{(x \times y) \times n}$, and solving n feature values $\lambda_1 \geq \lambda_2 \geq \ldots \geq \lambda_n \geq 0$ of the covariance matrix $\xi_{n \times n}$ and corresponding feature vectors $t_1, \ldots, t_m, \ldots t_n$;

Step 33C2, obtaining a score matrix $T_{n \times m}=(t_1, \ldots, t_m)$ of the principal components, wherein m is determined by formula $\Sigma_{k=1}^m \lambda_k/\Sigma_{k=1}^n \lambda_k \geq \delta_m$, $\delta_m \geq 85\%$; and Step 33C3, obtaining the principal component vectors $\Psi_{ij}=T_{n \times m}^T \cdot a_{ij}$ of the n-dimensional vectors $a_{ij}$, wherein m≤n, and $T_{n \times m}^T$ is a transposition of $T_{n \times m}$.

7. The air kerma conventional true value determining method of claim 6, wherein step 34 comprises the following steps:

Step 34A, obtaining a data matrix sample $(K_{ij},\Psi_{ij},K_j')_{(x \times y) \times (m+2)}$ via the experiments of the probes of the x sample dosimeters under the y kinds of $V_j$ conditions in step 32D, and obtaining a prediction model $K_{ij}=f_3(\Psi_{ij},K_j')$ of $K_{ij}$ by adopting a support vector machine regression method.

8. The air kerma conventional true value determining method of claim 7, wherein in step 34A, the specific method of obtaining a prediction model $K_{ij}=f_3(\Psi_{ij},K_j')$ of $K_{ij}$ by adopting a support vector machine regression method comprises the steps of: selecting radial basis function as a kernel function in the model training process, parameters of the kernel function are determined by a cross validation method; when the model is constructed, allocating the sample data $(K_{ij},\Psi_{ij},K_j')_{(x \times y) \times (m+2)}$ to training sets and testing sets according to a certain proportion; and when the test error is not more than 5%, ending the training, and determining the prediction model $K_{ij}=f_3(\Psi_{ij},K_j')$.

9. The air kerma conventional true value determining method of claim 8, wherein the certain proportion refers to that the proportion of the training set to the testing set is more than or equal to 1:1.

10. The air kerma conventional true value determining method of claim 9, wherein step 4 comprises the following steps:

Step 41, putting the reference point of the probe of the dosimeter being verified at the point of test;

Step 42, selecting a proper radiation source and putting it into an isotope radiation source accommodating device, and adjusting an attenuator to obtain the proper intensity $V_j$ of the incident ray beam; and Step 43, measuring the scattering gamma spectrum by using the gamma spectrometer, the scattering gamma spectrum is applied as input of the prediction model $K_{ij}=f_3(\Psi_{ij},K_j')=f_3[f_2(S_{ij}),K_j']=f_1(S_{ij},K_j')$ to obtain an air kerma conventional true value at the point of test in the MRR.

11. The air kerma conventional true value determining method of claim 8, wherein step 4 comprises the following steps:

Step 41, putting the reference point of the probe of the dosimeter being verified at the point of test;

Step 42, selecting a proper radiation source and putting it into an isotope radiation source accommodating device, and adjusting an attenuator to obtain the proper intensity $V_j$ of the incident ray beam; and Step 43, measuring the scattering gamma spectrum by using the gamma spectrometer, the scattering gamma spectrum is applied as input of the prediction model $K_{ij}=f_3(\Psi_{ij},K_j')=f_3[f_2(S_{ij}),K_j']=f_1(S_{ij},K_j')$ to obtain an air kerma conventional true value at the point of test in the MRR.

\* \* \* \* \*